(12) United States Patent
Calhoun et al.

(10) Patent No.: US 10,138,474 B2
(45) Date of Patent: Nov. 27, 2018

(54) SCAVENGER RECEPTOR UPTAKE FOR FABRY DISEASE ENZYME REPLACEMENT THERAPY

(71) Applicant: RESEARCH FOUNDATION OF THE CITY UNIVERSITY OF NEW YORK, New York, NY (US)

(72) Inventors: David H. Calhoun, Leonia, NJ (US); Lane Gilchrist, Brooklyn, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 61 days.

(21) Appl. No.: 13/970,551

(22) Filed: Aug. 19, 2013

(65) Prior Publication Data

US 2014/0050666 A1    Feb. 20, 2014

Related U.S. Application Data

(60) Provisional application No. 61/684,533, filed on Aug. 17, 2012.

(51) Int. Cl.
  *C12N 9/96* (2006.01)
  *A61K 9/127* (2006.01)
  *A61K 38/47* (2006.01)
  *A61K 49/00* (2006.01)
  *C12N 9/40* (2006.01)

(52) U.S. Cl.
  CPC .............. *C12N 9/96* (2013.01); *A61K 9/127* (2013.01); *A61K 38/47* (2013.01); *A61K 49/0043* (2013.01); *A61K 49/0056* (2013.01); *C12N 9/2465* (2013.01); *C12Y 302/01022* (2013.01); *C07K 2319/00* (2013.01)

(58) Field of Classification Search
  CPC ........ C12N 9/96; C12N 9/2465; A61K 9/127; A61K 38/47; A61K 49/0043; A61K 49/0056; C12Y 302/01022; C07K 2319/00
  See application file for complete search history.

(56) References Cited

U.S. PATENT DOCUMENTS

| | | | |
|---|---|---|---|
| 5,432,260 A * | 7/1995 | Stahl | C07K 7/06 424/193.1 |
| 7,011,831 B2 * | 3/2006 | Calhoun et al. | 424/94.61 |
| 2002/0127219 A1 * | 9/2002 | Okkels | A61K 38/24 424/94.61 |
| 2008/0260650 A1 * | 10/2008 | Tawakol et al. | 424/9.37 |
| 2012/0020878 A1 * | 1/2012 | Qi | 424/1.21 |

OTHER PUBLICATIONS

Bernard et al., Org. Biomol. Chem., 2016, 14, 4511.*

* cited by examiner

*Primary Examiner* — Robert S Cabral
(74) *Attorney, Agent, or Firm* — Hoffman & Baron, LLP (57) ABSTRACT

The present invention relates to a composition comprising a lysosomal enzyme conjugated to a negatively charged scavenger receptor ligand. In some embodiments, the lysosomal enzyme is conjugated to the scavenger receptor ligand by way of a linker. The present invention also relates to a composition comprising lysosomal enzyme encapsulated by a liposome, said liposome externally comprising a negatively charged scavenger receptor ligand. The invention further encompasses a method of treating a lysosomal storage disease with the compositions listed above. The invention further encompasses a method of treating a lysosomal storage disease with an acylated, acetylated, or aconitylated lysosomal enzyme.

39 Claims, 7 Drawing Sheets

SCAVENGER RECEPTOR UPTAKE FOR FABRY DISEASE ENZYME REPLACEMENT THERAPY

This application claims priority to U.S. Provisional patent application No. 61/648,533 filed Aug. 17, 2012, which is incorporated by reference in its entirety.

This invention was made with government support under RCMI RR03060 awarded by National Institutes of Health (NIH). The government has certain rights in the invention.

BACKGROUND OF THE INVENTION

Lysosomal storage diseases result from an inherited trait which affects the levels of enzymes in the lysosome. Approximately 30 lysosomal storage diseases are known to affect humans. Tay-Sach's disease and Gaucher disease are members of this group of diseases. Since specific pathways for the uptake of these other lysosomal enzymes also exist, enzyme replacement therapy is expected to be effective in Fabry disease and could logically be expected to be successful in these other diseases as well. Although these diseases are individually rare, (e.g., several thousand patients with Fabry disease are known to occur world wide, i.e., 1 to 40, 000), as a group this class of diseases accounts for a significant fraction of all inherited diseases.

Fabry disease is one such lysosomal storage disease known to affect humans. Fabry disease is an X-linked inborn error of metabolism resulting from a deficiency of the lysosomal enzyme, α-galactosidase A. Deficiency of α-galactosidase A results in the accumulation of its major glycosphingolipid substrate, globotriaosylceramide and related glycolipids with terminal α-galactosidic linkages. Progressive substrate deposition, especially in the plasma and vascular endothelium, leads to ischemia and infarction with early demise due to vascular disease of the heart, kidney, and brain.

Enzyme replacement therapy was first suggested by De Duve et al. (See De Duve et al. 1964, Federation Proceedings 23:1045) as a possible approach to the treatment of lysosomal storage defects such as Fabry disease. Several lines of evidence suggest that enzyme replacement therapy may be beneficial for patients with Fabry disease. For example, it has been demonstrated in cell cultures of fibroblasts obtained from patients with this disease that enzyme present in the culture medium is specifically transported to lysosomes. Clinical trials of enzyme replacement therapy have been reported for patients with Fabry disease using infusions of normal plasma (Mapes et al., 1970, Science 169: 987-989); α-galactosidase A purified from placenta (Brady et al., 1973 New Eng. J. Med. 279: 1163); or α-galactosidase A purified from spleen or a (Desnick et al., 1979, Proc. Natl. Acad. Sci. USA 76: 5326-5330). In one study (Desnick et al.) intravenous injection of purified enzyme resulted. in a transient reduction in the plasma levels of the substrate, globtriaosylceramide.

Since the initial studies of enzyme replacement therapy as a potential treatment for Fabry disease, Calhoun et al. have isolated human α-galactosidase A cDNA (Calhoun et al. 1985, Proc Natl Acad Sci USA 82:7364-8) and genomic clones (Quinn et al. 1987, Gene 58:177-88), and expressed the cDNAs in bacteria (Hantzopoulos et al. 1987, Gene 57:159-69), insect cells (Chen et al. 2000, Protein Expr Purif 20:228-36; Coppola et al. 1994, Gene 144:197-203), and Pichia pasioris (Chen et al. 2000, Protein Expr Purif 20:472-84). Furthermore, the purified recombinant α-galactosidase A produced in insect cells and P. pastoris has been shown to be taken up by Fabry fibroblasts in cell culture.

Several clinical trials of enzyme replacement therapy for Fabry disease patients in the last few years revealed clinical efficacy. Furthermore, the FDA has approved treatment of Fabry disease through intravenous administration of recombinant α-galactosidase A. This treatment methodology is known as enzyme replacement therapy (ERT). ERT does not affect the underlying defect, but provides a functional enzyme for the cell. Currently, two galactosidase drugs are available for treatment of Fabry disease via enzyme replacement therapy (ERT): agalsidase alfa (Replagal®, TKT/Shire) and agalsidase beta (Fahrazymne®, Genzyme). These protein based therapeutics are administered by (approved for) intravenous injection and deliver galactosidase activity to the lysomomes of affected organs in order to reduce the level of globotriaosylceramide accumulation.

However, the current approaches for enzyme replacement therapy can be expected to have limitations 88% of patients developed potentially neutralizing IgG antibodies to α-galactosidase A (Fabrazyme®) with a therapeutic enzyme dose of 1 mg per kilogram of body weight (Eng et al. 2001, N. Engl. J. Med. 345: 9-16); while only 21% developed antibodies with a lower dose of 0.2 mg of enzyme (Replagal®) per kilogram of body weight, (Schiffmann et al. 2001, JAMA 285:2743-9).

Fabry disease patients with adverse reactions to the infusions are currently treated with antihistamines and antipyretics, but it can be anticipated that life-long treatment required for these patients will lead to unacceptable levels of neutralizing antibodies. Furthermore, the treatment regimen is burdensome. Infusions typically involve a 4-6 hours session, in a hospital setting, every other week for life. In a recent clinical trial 14 out of 58 patients had to withdraw due to serious noncompliance, voluntary withdrawal, serious adverse events leading to death due to heart or kidney disease due to symptoms from the disease, and IgE antibody or positive skin tests. See Germain D P et al. 2007, J. Am. Soc. Nephrol., 18(5):1547-57. Most patients suffer from ill-defined infusion-associated reactions (vomiting, rigors, etc.) and are routinely pretreated with acetaminophen and hydroxyzine, and some patients require ibuprofen, prednisone, or both, for infusion associated reactions. Any improvement in treatment that leads to lower doses of enzyme, more effective therapeutic effects, or less frequent infusions would markedly improve the lives of Fabry disease patients and other patients reeving enzyme replacement therapy for lysosomal storage diseases.

Hence there exists a long standing need to provide a treatment regimen that requires lower doses of enzyme, thereby providing for snore effective therapeutic effects and less frequent infusions. In particular, there is a need to provide an enzyme therapeutic that allow for targeted delivery within the body and are sufficiently biologically active upon intracellular uptake.

SUMMARY OF THE INVENTION

The present invention relates to a composition comprising a lysosomal enzyme conjugated to a negatively charged scavenger receptor ligand. In some embodiments the lysosomal enzyme is an enzyme listed in TABLE 2, and the negatively charged scavenger receptor ligand is any ligand that binds a scavenger receptor and is transported to the lysosome.

In some embodiments, the lysosomal enzyme is conjugated to the scavenger receptor ligand by way of a linker.

The present invention also relates to a composition comprising lysosomal enzyme encapsulated by a liposome, said liposome externally comprising a negatively charged scavenger receptor ligand.

The invention further encompasses a method of treating a lysosomal storage disease with the compositions listed above.

The invention further encompasses a method of treating a lysosomal storage disease with an acylated, acetylated, or aconitylated lysosomal enzyme.

DETAILED DESCRIPTION

The present invention is generally directed to a composition and method relating to the enhanced delivery of lysosomal storage disease related agents to the lysosomes of cells affected by lysosomal storage disease.

In the following description, numerous specific details are set forth in order to provide a thorough understanding of the present embodiments. It will be apparent, however, to one having ordinary skill in the art that the specific detail need not be employed to practice the present embodiments. In other instances, well-known materials or methods have not been described in detail in order to avoid obscuring the present embodiments.

In one aspect, the invention relates to a composition that includes a lysozomal enzyme or an active fragment thereof, or the variant of said protein conjugated to a negatively charged scavenger receptor ligand.

A lysosomal enzyme as defined herein is any enzyme in the lysosome which hydrolyzes or metabolizes substrates in the lysosome. Lysozomal enzymes are commonly known. See TABLE 2, and www.ncbi.nlm.nih.gov/books/NBK6177/ (which is hereby incorporated by reference in its entirety). Examples of lysozomal enzymes include digestive enzymes such as glycosidases, proteases, and sulfatases. Examples of glycosidases include α-galactosidase A and heparinase. Examples of proteases include cathepsin K. Examples of sulfatases include iduronate sulfatase and N-acetyl glucosaminidase.

A lysosomal enzyme as defined herein to include an active fragment or variant thereof. By active fragments, or variants, is meant any part of the enzyme which is derived from the intact whole enzyme and still retains biological activity. Likewise, derivatives or variants of lysosomal enzyme mean enzymes which have been chemically modified or genetically engineered to effect minor changes, for example amino acid substitutions, which maintain biological activity.

In a preferred embodiment, the lysosomal enzyme is α-galactosidase A. α-galactosidase A is also a known protein. See ENZYME entry: EC 3.2.1.22, NCBI; and Calhoun et al. 1985, *Proc. Natl. Acad. Sci. USA* 82:7364-8. The α-galactosidase A protein is a lysosomal enzyme which hydrolyzes globotriaosylceramide and related glycolipids which have terminal α-galactosidase linkages. It is a 45 kDa N-glycosylated protein encoded on the long arm of the X chromosome. The initial glycosylated forms (Mr=55,000 to 58,000) synthesized in human fibroblasts or Chang liver cells are processed to a mature glycosylated form (Mr=50,000). The mature active enzyme as purified from human tissues and plasma is a homodimer. (Bishop et al. 1986, *Proc. Natl. Acad. Sci. USA* 83: 4859-4863).

A human liver cDNA for α-galactosidase A was identified in a λgt11 expression library (Calhoun et al., 1985, *Proc. Natl. Acad. Sci. USA* 82: 7364-7368), and its sequence reported by Bishop et al. The original cDNA isolated by Calhoun et al. (1985) encoded the mature amino acid sequence of α-galactosidase A. See Calhoun et al., 1985, *Proc. Natl. Acad. Sci. USA* 82: 7364-7368. These references are hereby incorporated by reference in its entirety.

α-galactosidase A can be derived from a natural source or be derived synthetically. In addition, α-galactosidase A, as defined herein can include an active fragment thereof, or include active variants. By active fragments, or variants, is meant any part of the enzyme which is derived from the intact whole enzyme and still retains biological activity. Likewise, derivatives or variants of lysosomal enzyme mean enzymes which have been chemically modified or genetically engineered to effect minor changes, for example amino acid substitutions, which maintain biological activity. As defined herein, biological activity of α-galactosidase A is the ability to hydrolyze globotriaosylceramide and related glycolipids which have terminal α-galactosidase linkages.

The α-galactosidase A utilized in the invention may be obtained using any method known to a person skilled in the art. It is thus possible to obtain the α-galactosidase A, a fragment thereof, or the variant of said protein by any standard method. For example, α-galactosidase A may be obtained from cDNA by means of expression in a heterologous organism such as, for example, *Escherichia coli, Sacharomyces cerevisiae, Pichia pastoris*. For example, U.S. Pat. No. 5,658,567 to Calhoun et al. describes a method of obtaining recombinant α-galactosidase A; which is herein incorporated by reference in its entirety. Additional information may be found in U.S. Pat. Nos. 5,179,023; 6,461,609; and 7,011,831, each of which is hereby incorporated by reference in its entirety.

In another embodiment, the lysosomal enzyme may be acylated. Acylation of lysosomal may be accomplished by any standard method. For example, acylation of amino groups in proteins may be accomplished with acid anhydrides. Suitable acid anhydrides include, for example, citraconic anhydride, maleic anhydride, succinic anhydride, 3-hydroxyphthalic anhydride, trimellitic anhydride, methyltetrahydrophthalic anhydride, cis-aconitic anhydride, fatty acid anhydrides, hexahydrophthalic anhydride, and phthalic anhydride.

In another embodiment, the lysosomal enzyme may be acetylated. Acetylation of lysosomal enzyme may be accomplished by any standard method. For example, reacting the protein of interest with acetic anhydride or acetyl chloride.

In another embodiment, the lysosomal enzyme may be aconitylated. Aconitylation of lysosomal enzyme may be accomplished by any standard method. For example, reacting the protein of interest with cis-aconitic anhydride.

The lysosomal enzyme is conjugated to a charged scavenger receptor ligand (SRL). SRLs are commonly known in the art. SRLs are defined as any ligand that is capable of binding scavenger receptors and the resulting ligand undergoes receptor-mediated endocytosis leading to the degradation of ligand in the lysosome. For example, SRLs include, without limitation: polyanionic ligands, AcLDL, OxLDL, β-amyloid, molecular chaperones, ECM, AGE, apoptotic cells, activated B-cells, bacteria, HDL, LDL, OxLDL, VLDL, AGE, ECM, activated platelets, serum protein, BSA, and HSA. See TABLE 1 and Stephen et al. 2010, *Int. J. Hypertens.*, 646929. This publication is incorporated herein by reference in its entirety.

LDL is low density lipoprotein; VLDL, very low density lipoprotein; AcLDL is acetylated-low density lipoprotein; and OxLDL is oxidized-low density lipoprotein. HDL is high density lipoprotein.

β-amyloid is a peptide of 36-43 amino acids that is processed from the amyloid precursor protein (APP). This peptide is characterized as having the central sequence KLVFFAE. The core sequence can be present once or several times in a β-amyloid peptide.

Molecular chaperones are proteins that assist the non-covalent folding or unfolding and the assembly or disassembly of other macromolecular structures. Examples include heat shock proteins (Hsp70, Hsp90 and Hsp110), gp96 and calreticulin.

ECM is extracellular matrix. These ligands comprise components of the extracellular matrix, for example, glycated collagen IV.

AGE advanced glycation end products. AGE are a heterogeneous group of compounds linked to both oxidative stress and inflammation and they are found in many tissues. They are the result of modifications of proteins or lipids that become nonenzymatically glycated and oxidized after contact with aldose sugars. Some examples of these ligands include glycated hemoglobin A1c (HbA1c).

Apoptotic cells are cells that are undergoing or about to undergo apoptosis. One characteristic of apoptotic cells is increased phosphatidylserine (PS) on the cell surface as compared to non-apoptotic cells.

Activated B-cells, are B-cells that have undergone the binding of antigen to receptors on its cell surface which causes the cell to divide and proliferate.

Bacteria are unicellular organisms. Examples include *Staphylococcus aureus, Neisseria meningitides, Streptococcus pyogenes* and *Escherichia coli.*

Activated platelets are platelets which react to injury. For example, when the skin is broken, platelets are exposed to collagen, which causes them to activate. Platelet activation triggers the release of chemicals which cause additional platelets to activate.

Serum protein of the present invention is commonly known in the art. Total serum protein, purified serum protein components, or any combination of serum proteins may be used. In a preferred embodiment, bovine serum albumin (BSA) or human serum albumin (HSA) may be used. Serum proteins are commercially available from Sigma Aldrich. In a preferred embodiment, the SRL is serum protein. In another preferred embodiment, the SRL is human serum albumin (HSA).

TABLE 1

Scavenger Receptor Ligands and Expression profiles.

| Class | Scavenger receptor | Ligands | Expression profile | Involvement in CVD? |
|---|---|---|---|---|
| A | SR-A | AcLDL, OxLDL, β-amyloid, molecular chaperones, ECM, AGE, apoptotic cells, activated B-cell, bacteria | Macrophages, mast, dendritic, endothelial and smooth muscle cells | Yes - involved in OxLDL uptake by macrophages leading to foam cell formation |
| A | MARCO | AcLDL, OXLDL, apoptotic cells, B cells, bacteria | Macrophages, dendritic cells | No |
| B | SR-B | HDL, LDL, OxLDL, apoptotic cells | Monocytes/macrophages, hepatocytes and adipocytes | Reduces atherosclerosis through reverse cholesterol transport of HDL |
| B | CD36 | AcLDL, OxLDL, HDL, LDL, VLDL, β-amyloid, AGE, apoptotic cells | Macrophages, platelets, adipocytes, epithelial and endothelial cells | Yes - OxLDL uptake into macrophages leading to foam cell formation |
| E | LOX-1 | OxLDL, molecular chaperones, ECM, AGE, apoptotic cells, activated platelets, bacteria | Endothelial and smooth muscle cells, macrophages, and platelets | Yes - OxLDL uptake in endothelial cells, leads to endothelial dysfunction |
| F | SRECI/II | AcLDL, OxLDL, molecular chaperones, apoptotic cells | Endothelial cells and macrophages | Low levels of AcLDL uptake |
| G | SR-PSOX | OxLDL and bacteria | Macrophages, smooth muscle, dendritic, endothelial cells, and β- and T cells. | Yes - involved in OxLDL uptake in macrophages |
| H | FEEL-I/II | AcLDL, molecular chaperones, ECM, AGE, bacteria | Monocytes/macrophages, endothelial cell | No known link |

SR-A: scavenger receptor class A,
AcLDL: acetylated low density lipoprotein,
OxLDL: oxidised low density lipoprotein,
ECM: extracellular matrix,
AGE: advanced glycation and products,
MARCO: macrophage receptor with collagenous structure,
HDL: high density lipoprotein,
LDL: low density lipoprotein.
VLDL: very low density lipoprotein,
LOX-1: lectin-like oxidized low density lipoprotein receptor-1,
FEEL-I/II: fascidin, epidermal growth factor (EGF)-like, laminin-type EGF-like, and link, domain-containing scavenger receptor-1.

In another preferred embodiment, the SRL is any ligand that binds to a Scavenger Receptor (SR) and undergoes receptor-mediated endocytosis leading to the delivery of ligand to the lysosome. Scavenger receptors are commonly known in the art. TABLE 1 sets forth different classes of known ligands and the scavenger receptor to which they bind. Scavenger Receptors (SR) are defined as a family of molecules sharing the ability to bind polyanionic ligands. For example, scavenger receptors include, without limitation, SR-AI; MARCO; SRCL; CD36; dSR-Cl; CD68; LOX-1; SREC-I; SREC-II; SR-PSOX FEEL-1, FEEL-2, CSR1, SCSRA5, SR-B1, LIMP2, SR-PSOX, CD163, CD163L1, CD5, and CD6. See TABLE 1, and Murphy et al. 2005, *Atherosclerosis* 182, 1-15. This publication is incorporated herein by reference in its entirety.

The SRLs conjugated to the lysosomal enzyme are negatively charged. Said negative charge may be naturally occurring, or conferred by chemical modification by any method known in the art. For example, said negative charge can be conferred by formaldehyde treatment. In another embodiment, the SRL may be oxidized by chemical modification by any method known in the art. For example, with treatment by $Cu^{2+}$.

In another embodiment, the SRL may be acylated. Acylation of SRL may be accomplished by any standard method. For example, acylation of amino groups in proteins may be accomplished with acid anhydrides. Suitable acid anhydrides include, for example, citraconic anhydride, maleic anhydride, succinic anhydride, 3-hydroxyphthalic anhydride, trimellitic anhydride, methyl-tetrahydrophthalic anhydride, cis-aconitic anhydride, fatty acid anhydrides, hexahydrophthalic anhydride, and phthalic anhydride.

In another embodiment, the SRL may be acetylated. Acetylation of lysosomal enzyme may be accomplished by any standard method. For example, reacting the protein of interest with acetic anhydride or acetyl chloride.

In another embodiment, the SRL may be aconitylated. Aconitylation of lysosomal enzyme may be accomplished by any standard method. For example, reacting the protein of interest with cis-aconitic anhydride by any standard method.

Conjugation of lysosomal enzyme to a SRL may be accomplished by any standard method commonly known in the art. For example, a lysine on a lysosomal enzyme may be modified with an adaptor molecule to introduce a reactive group, such as a thiol. For example, the lysine residue may be reacted with a thiolation reagent, such as N-succinimidyl S-acetylthioacetate (SATA) or 2-iminothiolane. The thiol (deprotected thiol in the case of SATA) may be reacted with the thiol group on the side chain of cysteine on the surface of a SRL.

In a further example, a cysteine on the surface of a SRL may be modified with an adaptor molecule to introduce a reactive group, such as a N-hydroxysuccinimide (NHS). For example, the cysteine residue may be reacted with Sulfosuccinimidyl-4-(N-maleimidomethyl) cyclohexane-1-carboxylate (Sulfo-SMCC). The modified amino acid residue may then be reacted with the amino groups of lysines on a lysosomal enzyme to form a SRL—lysosomal enzyme conjugate.

Other conjugation techniques and strategies commonly known in the art may be used. Further conjugation techniques and strategies commonly known in the art are described in Hermanson, G., T. *Bioconjugate Techniques, Second Edition;* Academic Press: San Diego, Calif., 2008; which is herein incorporated by reference in its entirety.

In another aspect of the invention, the scavenger receptor ligand is conjugated to a lysosomal enzyme by way of a linker. The linker serves to covalently bind the lysosomal enzyme to the negatively charged scavenger receptor ligand. Any linker commonly known in the art may be used. In a preferred embodiment, the linker is non-absorbing, soluble, and hydrophilic linker. Non-absorbing is defined as being as a characteristic wherein the linker does not non-specifically bind protein, or does not illicit an immune reaction.

In another embodiment, the linker comprises a polysaccharide. An example of polysaccharide linker includes: hyaluronate, hyaluronic acid, heparin, chondroitin sulfate, chitosan, cellulose, dextran and alginic acid.

In another embodiment, the linker comprises a polyamine.

In another embodiment, the linker comprises poly(glycerol) (PG) and hyperbranched PG(HPG); poly(2-oxazoline)s, include poly(2-methyl-2-oxazoline (PMeoX) and poly(2-ethyl-2-oxazoline (PEtOX); poly(acrylamide), poly (vinylpyrrolidone (PVP), and poly (N-(2-hydroxypropyl) methacrylamide (PHPMA).

In another embodiment, the linker comprises a polyamino acid. For example, a polyamino acid may comprise poly glutamic acid (PGA); poly(hydroxyethyl-L-asparagine (PHEA); and poly(hydroxyethyl-L-glutamine (PHEG).

In another embodiment, the linker comprises polyethylene glycol (PEG). Some examples of PEG include linear or branched (multi-arm or star) structures.

Examples of multi-arm PEG polymers include comb and brush PEG polymers. A comb PEG is a branched PEG comprising two or more three-way branch points and linear side chains emanating from a main backbone polymer chain. A brush PEG is a branched PEG comprising three or more linear polymer chains emanating from a main backbone polymer chain.

In another preferred embodiment, the linker is star PEG. A star PEG, without limitation, is a branched PEG comprising three or more linear polymer chains emanating from a central core group or a single branch point. Examples of star shaped PEG polymers include, without limitation, 3, 4, 5, 6, 7, 8, 9, 10, and 11-arm star PEG polymers. PEG linkers are commonly known in the art and are commercially available from several commercial vendors including Sigma-Aldrich, NANOCS, and Creative PEGWorks.

In standard nomenclature, a branched PEG can be referred to by the number of polymer chains. Thus, a branched PEG having three polymer chains is referred to as a three-arm PEG or 3-arm PEG, a branched PEG having four polymer chains is referred to as a four-arm PEG or 4-arm PEG, a branched PEG having five polymer chains is referred to as a five-arm PEG or 5-arm PEG, a branched PEG having six polymer chains is referred to as a six-arm PEG or 6-arm PEG, a branched PEG having seven polymer chains is referred to as a seven-arm PEG or 7-arm PEG, etc. The physical properties of PEG, such as melting point, cohesiveness, and viscosity, can be altered by varying the length of the polymer chain, the type of initiator used during the polymerization process, and/or whether the PEG has a linear or branched configuration. PEG molecules, both linear and branched, are commercially available over a wide range of molecular weights from 300 g/mol to 10,000,000 g/mol.

Multi-arm polyethylene glycol is advantageous over the linear (straight-chain) polyethylene glycol in that multiarm PEG allows for a plurality of substituents. Straight-chain polyethylene glycol derivatives with two functional groups can only carry two molecules, while the multi-arm polyethylene glycol has several end groups, and thus has more than one active molecule connection points, and can carry several similar or different molecules.

Figure 1:
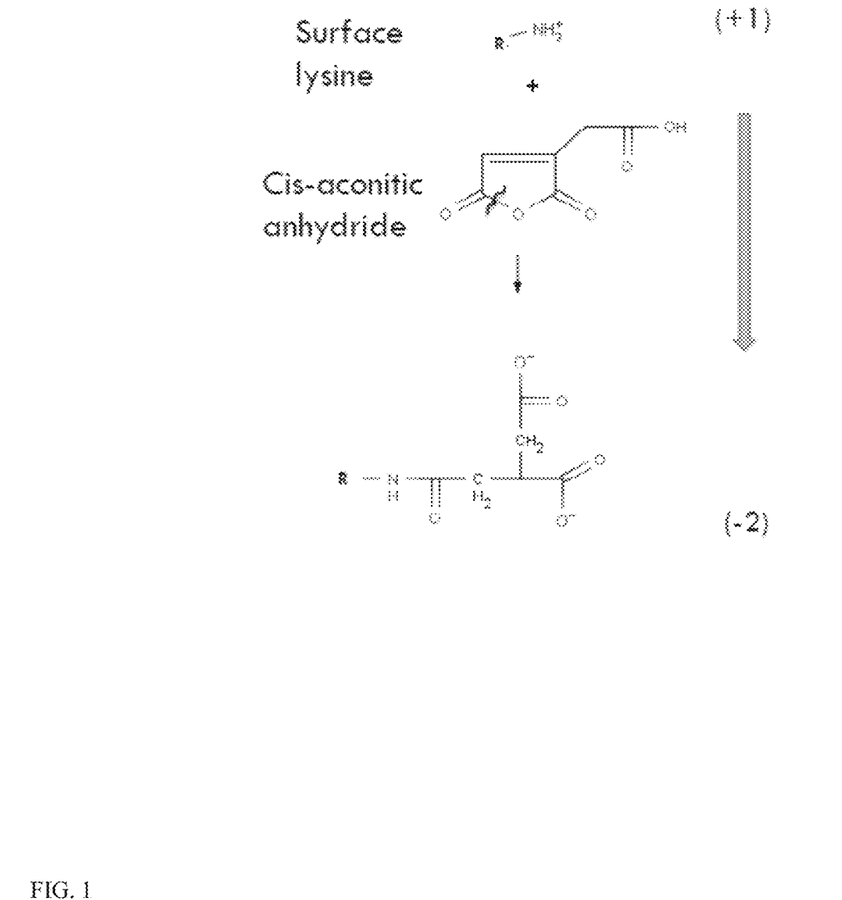
FIG. 1 depicts the reaction between cis-aconitic anhydride and an amino group of a surface exposed lysine.
Figure 2:
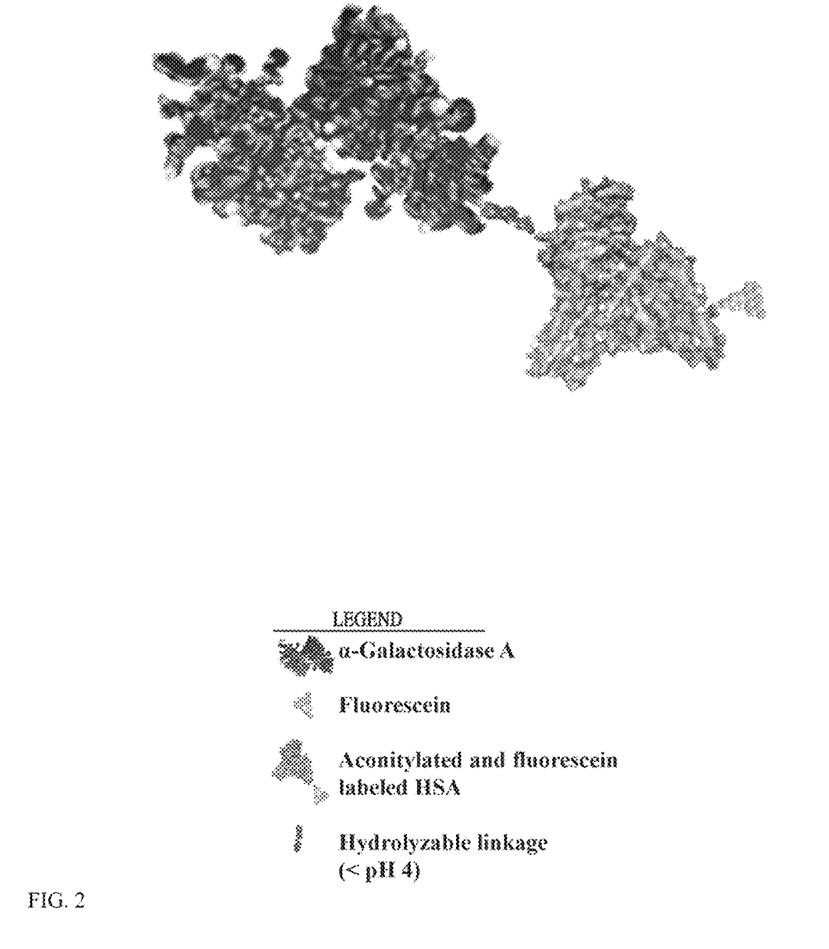
FIG. 2 depicts α-galactosidase A with hydrolyzable polymer linkage to acylated and labeled human serum albumin.
Figure 3:
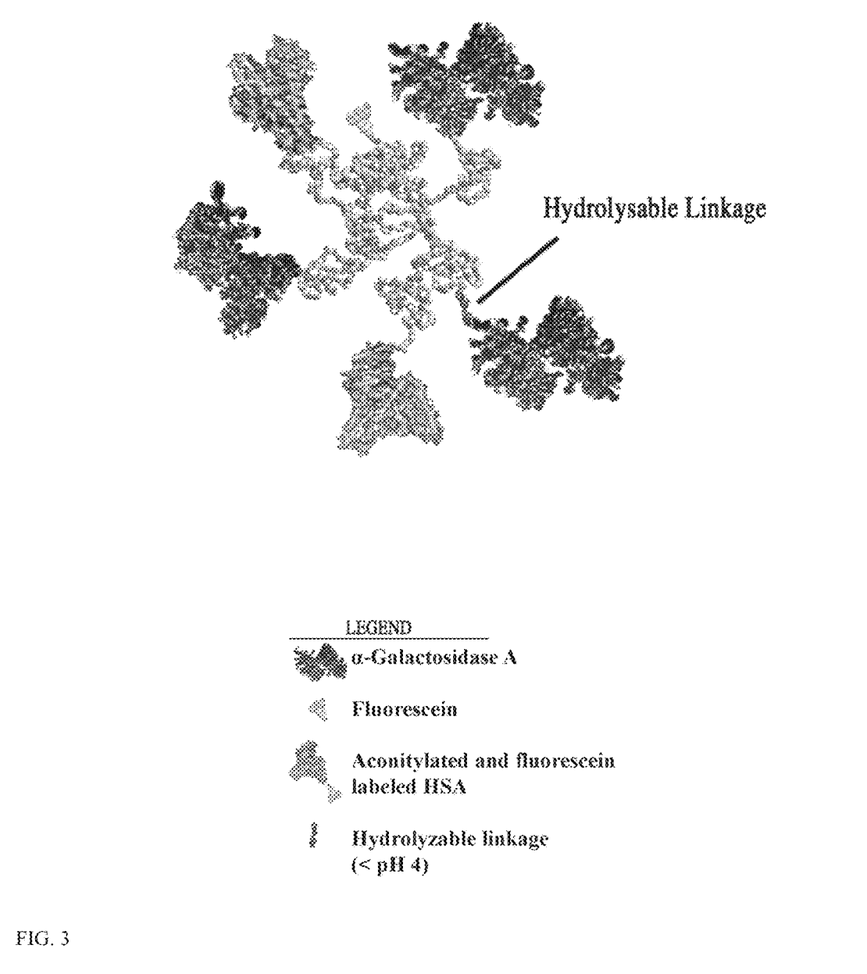
FIG. 3 depicts α-galactosidase A linked to 8-arm PEG with targeting and fluorescent group.
Figure 4:
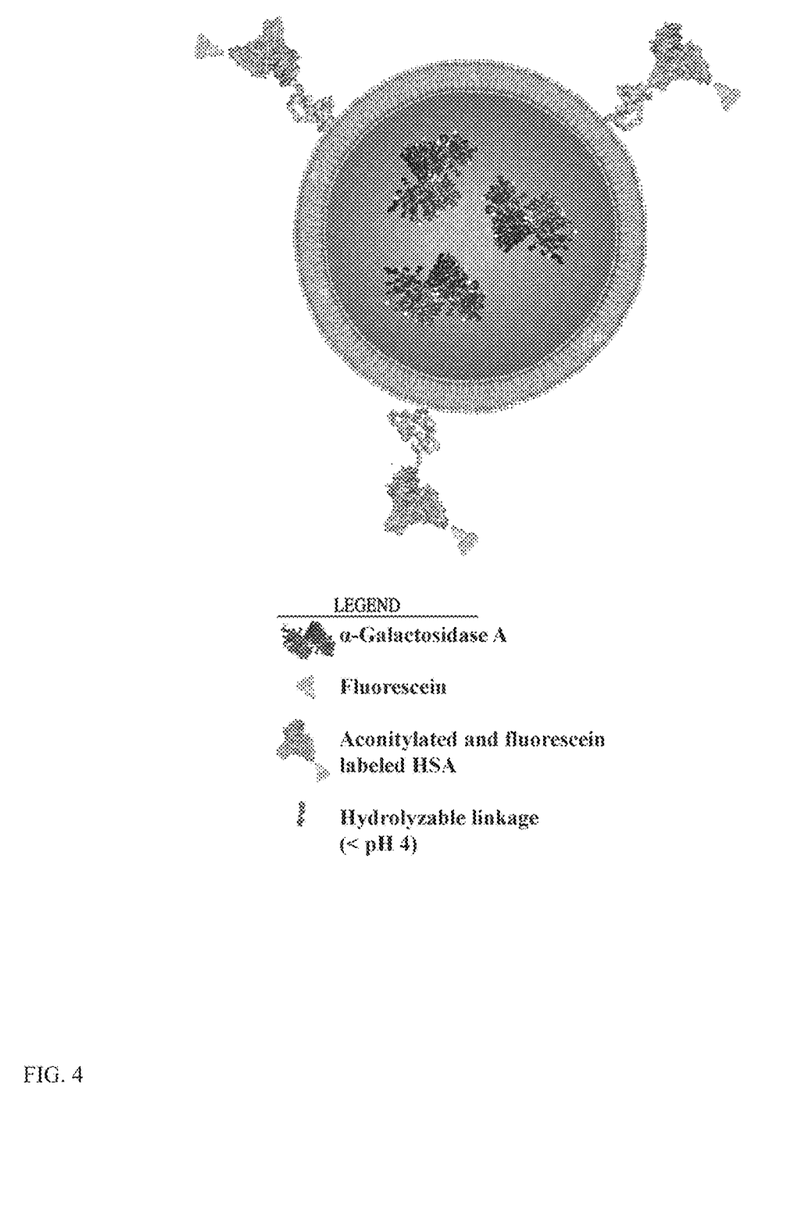
FIG. 4 depicts α-galactosidase A encapsulated in liposome with external surface conjugated with fluorescently labeled and aconitylated-HSA.
Figure 5:
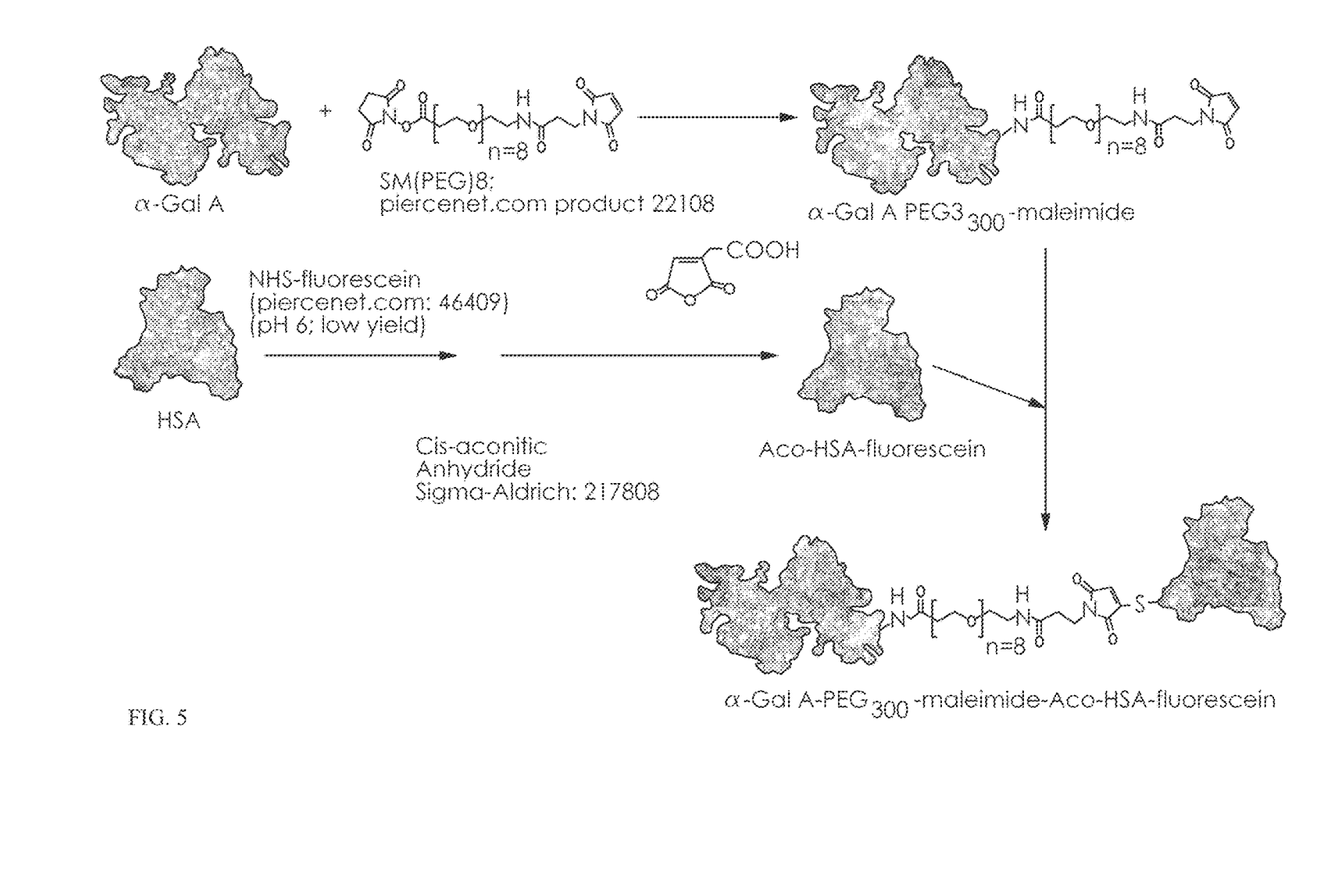
FIG. 5 depicts α-galactosidase A coupled to fluorescently labeled, aconitylated-HSA.
Figure 6:
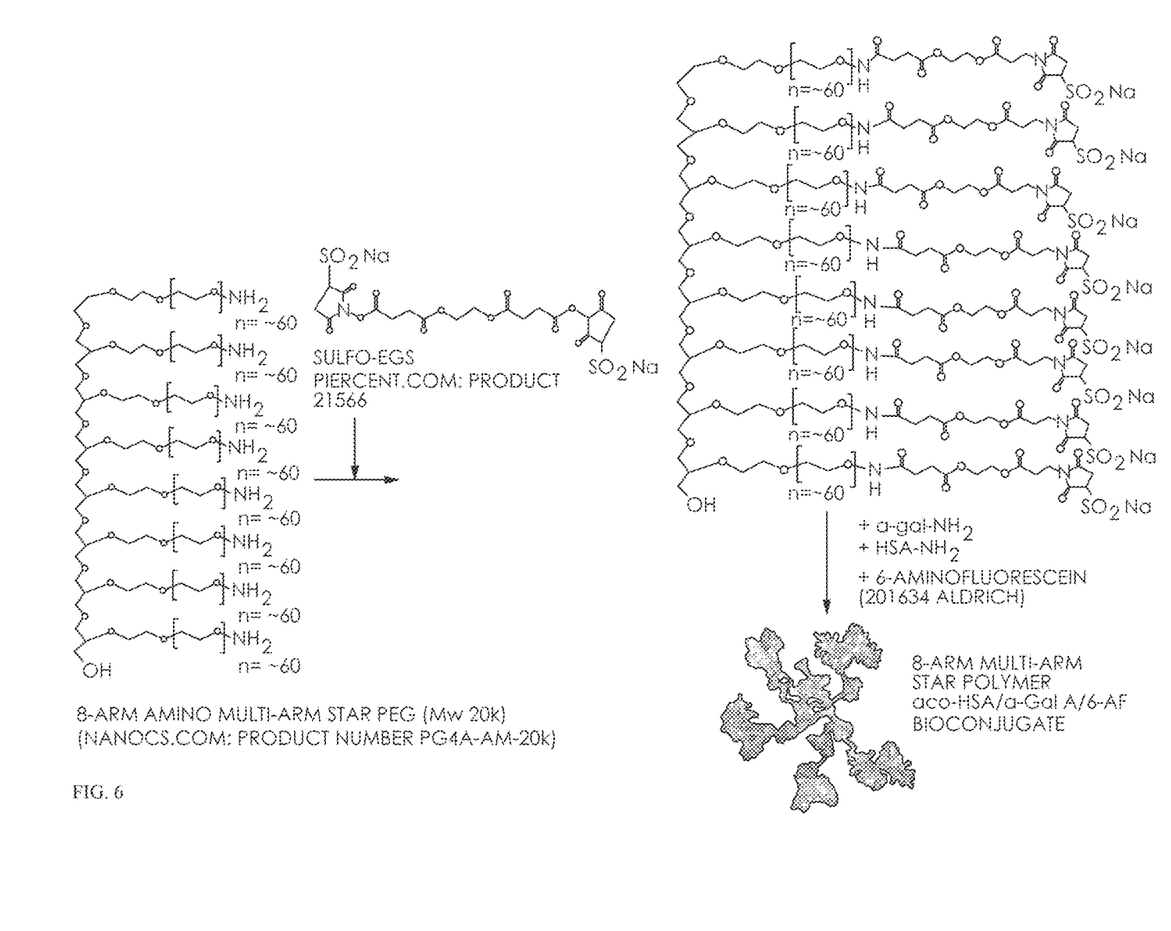
FIG. 6 depicts α-galactosidase A and fluorescently labeled, aconitylated-HSA coupled to multi-arm PEG (amino based coupling).
Figure 7:
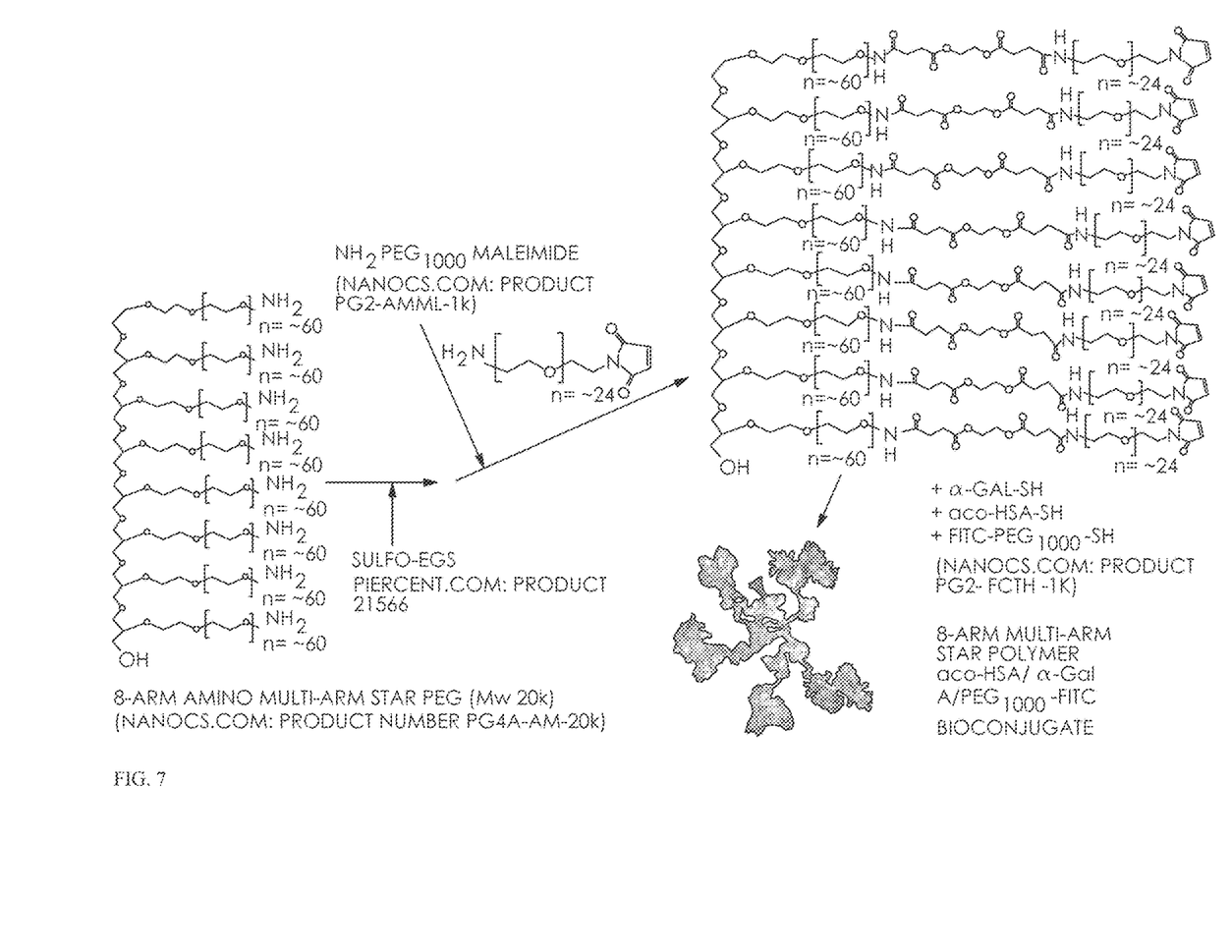
FIG. 7 depicts α-galactosidase A and fluorescently labeled, aconitylated-HSA coupled to multi-arm PEG (sulfhydryl "CYS"-based coupling).

The composition comprising the lysosomal enzyme-PEG-SRL assemblies/compositions may be synthesized by any method commonly known in the art. For example a linear PEG linker may be functionalized with NHS and maleimide termini; and conjugated to the primary amines on lysosomal enzyme via the NHS functional group and the thiol groups on the SRL via the maleimide functional group. In a further example, amino functionalized multi-arm star PEG may be reacted with ethylene glycolbis (sulfosuccinimidylsuccinate) (Sulfo-EGS), thereby creating a sulfo-NHS ester functionalized star PEG that may react with amino groups on lysosomal enzyme and SRL. The functionalized star PEG molecule may be reacted with lysosomal enzyme, SRL, and a functionalized fluorophore to create a composition wherein the termini of the star PEG independently comprise lysosomal enzyme, SRL, and a label. An example is depicted in FIG. 3.

When the lysosomal enzyme is α-galactosidase A, α-galactosidase A may be bound to galactose to block disruption of the catalysis. FIG. 3 is provided as an example only, and the composition may comprise different numbers of α-galactosidase A, serum protein, and a label; it may include α-galactosidase A and serum protein only; the serum protein may or may not be labeled.

In another embodiment, lysosomal enzyme is linked to the scavenger receptor ligand by way of a hydrolysable linker. Hydrolysable linkers, or pH labile linkers, are designed to be broken down only in the acidic environment of the lysosome. Other suitable linkers include disulfide-based linkers, which are broken down in the cell where there is a high concentration of thiols, and peptide linkers, which are broken down by intracellular enzymes. Hydrolysable linkers are commonly known in the art. For example, linkers containing amide, hydrazine, or cis-aconityl bonds.

In another embodiment, the composition of the invention further comprises a label. Labels are commonly known in the art. For example, suitable labels include: biotin, enzyme conjugates, and fluorescent.

In preferred embodiment, lysosomal enzyme-acylated SRL conjugate or the lysosomal enzyme-linker-SRL comprises a fluorescent label. Fluorescent labels are commonly known in the art. Suitable fluorescent labels include: fluorescein, rhodamine, coumarin, BODIPY, cascade blue, Lucifer yellow, phycobliprotein, cyanine, lanthanide, quantum dot nanocrystals, and derivatives thereof.

In another embodiment, the fluorescent label is conjugated to the SRL. Conjugation of the fluorescent label to the SRL may be accomplished by any method commonly known in the art. For example, a NHS-functionalized fluorphore may react with an amine group of the SRL.

In another embodiment of the invention, the fluorescently labeled SRL is aconitylated.

In another embodiment, a heterofunctional PEG with a NHS functional group at one termini and a maleimide functional group at another termini is first reacted with an amino group on a lysosomal enzyme; and then reacted with a thiol group on the SRL. In another aspect of the invention, α-galactosidase A is the lysosomal enzyme and may be bound to galactose to block disruption of the catalysis.

In a another aspect of the invention, a composition is provided that includes comprising lysosomal enzyme as defined above encapsulated by a liposome, said liposome externally comprising SRL.

Encapsulation of substrates by liposomes is commonly known in the art. For example, the composition of the invention may generally be prepared by the process of combining a lipid composition with a solution of human lysozymal enzyme or an active fragment or derivative thereof, suspension or mixture under conditions suitable for liposome formation with the desired amount of a lysosomal enzyme or an active fragment or derivative thereof encapsulated therein.

For example, liposomes may be generated by first assembling a lipid bilayer formulation comprising 5 mole % DSPE-PEG(2000) maleimide, 94% L-α-phosphatidylcholine (POPC), and 1% DiO lipid tracer (1,1'-dioctadecyl-3,3,3',3'-tetramethylindodicarbocynanine) to make dried lipid film at 25° C. from chloroform solution. Hydrate 2 mg/ml lipid film in PBS buffer with 2 mg/ml lysosomal enzyme to give loaded multilamellar vesicles, then form 100 nm nominal diameter liposomes by probe sonication. Formed liposomes may range from 30 nm to 1 um in diameter. In a preferred embodiment, the liposomes are 100 nm. In another preferred embodiment, the liposomes are 200 nm. In another preferred embodiment, the liposomes are 300 nm. Unencapsulated lysosomal enzyme is removed by G-100 Sephadex chromatography.

Formed liposomes may then be conjugated with aconitylated SRL fluorescein by surface maleimide groups. 3 mg/ml of HSA and 2 mg/ml liposomes are incubated at pH 7 and 4° C. A final purification is performed with a G-100 Sephadex column to remove free aconitylated SRL fluorescein.

Further liposome preparation techniques commonly known in the art and are described in Liposomes: A Practical Approach, edited by V. P. Torchilin, Volkmar Weissig Oxford University Press, USA, 2nd edition 2003); which is herein incorporated by reference in its entirety.

The liposome containing the encapsulated human lysosomal enzyme or an active fragment or derivative thereof may be coated with negatively charged SRL using methods commonly known in the art. For example, free thiol from surface cysteines on the SRL is reacted with maleimide groups present on the surface of the liposome (described above) to form a composition comprising SRL bound to the surface of liposomes.

The SRL as used herein, refers to any of the SRL described above.

In a further embodiment of the invention the acylated SRL may be covalently labeled. The label may be fluorescent or nonfluorescent. Such labels are commonly known in the art, and are described herein.

In a further embodiment of the invention, the SRL may be acylated, acetylated or aconitylated. Such chemical modifications are commonly known in the art, and are described herein. In a embodiment, the SRL is HSA.

In another embodiment, the SRLs are negatively charged. Said negative charge may be naturally occurring, or conferred by chemical modification by any method known in the art. For example, said negative charge can be conferred by formaldehyde treatment. In another embodiment, the SRL may be oxidized by chemical modification by any method known in the art. For example, with treatment by $Cu^{2+}$.

Further liposome preparation techniques commonly known in the art and are described in Liposomes: A Practical Approach, edited by V. P. Torchilin, Volkmar Weissig Oxford University Press, USA, 2nd edition 2003); which is herein incorporated by reference in its entirety.

Methods of Use

In another aspect of the invention, a method is provided for the treatment of a lysosomal storage disease. The method includes administering a composition that includes a lysosomal enzyme conjugated to a negatively charged scavenger receptor ligand, as described above, to a mammal in need thereof. In one embodiment, the lysosomal storage disease is caused by deficient lysosomal enzyme. In this specification "treating" refers to inhibiting disease; preventing disease; aiding in the prevention of disease, or combinations thereof.

Deficient lysosomal enzyme is defined as any disease state resulting from the absence of a lysosomal enzyme, deficiency of the enzyme, a non-functional enzyme, or an enzyme with reduced functionality. An enzyme with reduced functionality is defined as an enzyme whose catalytic activity is less than wild type enzyme.

In lysosomal storage diseases, the reduced functionality of the lysosomal enzyme causes a buildup of substrate in the lysosome, such as lipids and glycoproteins. The accumulation of substrate causes the cell to malfunction. Symptoms of lysosomal storage disease can be mild to severe and can include developmental delay, movement disorders, seizures, deafness, and/or blindness. Various lysosomal storage diseases are known in the art. TABLE 2 provides for a list of lysosomal storage diseases and the protein responsible for that disease.

In another aspect of the invention, the method includes administering acylated, acetylated, or aconitylated lysosomal enzyme to a mammal in need thereof.

In preferred embodiment of the invention, the lysosomal enzyme is α-galactosidase A, and the disease is Fabry disease.

TABLE 2

PROTEIN AND CORRESPONDING LYSOSOMAL STORAGE DISEASE

| LYSOSOMAL PROTEIN | LYSOSOMAL STORAGE DISEASE |
|---|---|
| α-galactosidase A | Fabry |
| α-sialidase | sialidosis |
| α-mannosidase | α-mannosidosis |
| β-mannosidase | β-mannosidosis |
| glycosylasparaginase | aspartylglucosaminuria |
| α-fucosidase | fucosidosis |
| α-N-acetylglucosaminidase | Schindler |
| β-galactosidase | GM1-gangliosidosis (MPS IVB |
| β-Hexosaminidase α-subunit | GM2-gangliosidosis (Tay-Sachs) |
| β-Hexosaminidase β-subunit | GM2-gangliosidosis (Sandhoff) |
| GM2 activator protein | GM2-gangliosidosis |
| Glucocerebrosidase | Gaucher disease |
| Saposin C | Gaucher disease |
| Arylsulfatase A | Metachromatic leukodystrophy |
| Saposin B | Metachromatic leukodystrophy |
| Formyl-Glycine generating enzyme | Multiple sulfatase deficiency |
| β-Galactosylceramidase (Krabbe) | Globoid cell leukodystrophy |
| Iduronate sulfatase | MPS II (Hunter) |
| α-Iduronidase | MPS 1 (Hurler, Scheie) |
| Heparan N-sulfatase | MPS IIIa (Sanfilippo A) |
| Acetyl-CoA transferase | MPS IIIc (Sanfilippo C) |
| N-acetyl glucosaminidase | MPS IIIb (Sanfilippo B) |
| β-glucuronidase | MPS VII (Sly) |
| N-acetyl glucosamine 6-sulfatase | MPS IIId (Sanfilippo D) |
| N-Acetylgalactosamine 4-sulfatase | MPS VI |
| Galactose 6-sulfatase | MPS IVA (Morquio A) |
| Hyaluronidase | MPS IX |
| α-Glucosidase | Pompe |
| Acid sphingomyelinase | Niemann Pick type A and B |
| Acid ceramidase | Farber lipogranulomatosis |
| Acid lipase | Wolman and cholesteryl ester storage disease |
| Cathepsin K | Pycnodystostosis |
| Tripeptidyl peptidase | Ceroide lipofuscinosis 2 |
| Palmitoyl-protein thioesterase | Ceroide lipofuscinosis 1 |

The method of the invention includes administering an effective amount of the composition to the mammal in need thereof. Preferably the mammal is a human. An effective amount is defined as an amount sufficient to reduce, prevent, or inhibit the accumulation of lysosomal enzyme substrate in the lysosomes of cells of the mammal. Suitable examples of mammals other than humans include, for example, rabbits, rats, mice, horses, goats, or primates.

A therapeutically effective amount of the composition of the invention as described above may range from about 50 to about 10,000 units enzyme activity per kg body weight per day. For example, when the lysosomal enzyme is α-galactosidase A, a unit of α-galactosidase A activity corresponds to one nanomole of 4-methylumbelliferyl-α-D-galactopyranoside hydrolyzed per hour at 37° C. See Calhoun et al., 1985, Proc. Natl. Acad. Sci. USA 82: 7364-7368. This reference is hereby incorporated by reference in its entirety.

In a preferred embodiment, the therapeutic amounts from about 1 μg to about 2000 μg per kg of body weight per day. The dosage regimen may be adjusted to provide the optimum therapeutic response. For example, several divided doses may be administered daily or the dose may be proportionally reduced as indicated by the exigencies of the therapeutic situation.

A practical advantage is that the active compound may be administered in a convenient manner such as by the oral, intravenous (where water soluble), intramuscular, intravenous, intranasal, intradermal, subcutaneous, or suppository routes. Depending on the route of administration, the active ingredients of the composition of the invention as described above containing pharmaceutical composition may be required to be coated in a material to protect said ingredients from the action of enzymes, acids or other natural conditions.

The active compounds may also be administered parenterally or intraperitoneally. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must preserved against the contaminating action of microorganisms such as bacteria and fungi. The carrier may be a solvent or dispersion medium containing, for example, water, ethanol, polyol (for example, glycerol, propylene glycol, and polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. The preventions of the action of microorganisms may be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions may be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filter sterilization.

Generally, dispersions are prepared by incorporating the various sterilized active ingredients into sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

The composition of the invention as described above may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparation should contain at least 1% of active compound. The percentage of the compositions and preparations may, of course, be varied and may conveniently be between about 5 to about 80% of the weight of the unit. The amount of active compound in such therapeutically useful compositions is such that a suitable dosage is obtained. A suitable dosage is any dosage sufficient to achieve a beneficial outcome. Preferred compositions or preparations according to the present invention are prepared so that an oral unit dosage form contains between about 10 μg and 1000 μg of active compound.

The tablets, troches, pills, capsules and the like may also contain the following: A binder such as gum agragacanth, acacia, corn starch or gelatin; excipients such as dicalcium phosphate; a disintegrating agent such as corn starch, potato starch, alginic acid and the like; a lubricant such as magnesium stearate; a sweetening agent, such as sucrose, lactose or saccharin or a flavoring agent such as peppermint, oil of wintergreen, or cherry flavoring. When the dosage form is a capsule, it may contain, in addition to materials of the above type, a liquid carrier. Various other materials may be present as coatings or to otherwise modify the physical form of the unit dosage. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

It is especially advantageous to formulate parenteral compositions in dosage unit form for ease of administration and uniformity of dosage. Unit dosage form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health impaired as herein disclosed in detail.

The composition of the invention as described above, is compounded for convenient and effective administration in pharmaceutically effective amounts with a suitable pharmaceutically acceptable carrier in dosage unit form as hereinbefore disclosed. A unit dosage is any dosage sufficient to achieve a beneficial outcome. A unit dosage form can, for example, contain the principal active compound in amounts ranging from 10 μg to about 1000 μg. Expressed in proportions, the active compound is generally present in from about 10 μg to about 1000 μg/ml of carrier. In the case of compositions containing supplementary active ingredients, the dosages are determined by reference to the usual dose and manner of administration of the said ingredients.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredient, its use in the therapeutic compositions is contemplated. Supplementary active ingredients may also be incorporated into the compositions.

Reference throughout this specification to "one embodiment", "an embodiment", "one example" or "an example" means that a particular feature, structure or characteristic described in connection with the embodiment or example is included in at least one embodiment of the present embodiments. Thus, appearances of the phrases "in one embodiment", "in an embodiment", "one example" or "an example" in various places throughout this specification are not necessarily all referring to the same embodiment or example. Furthermore, the particular features, structures or characteristics may be combined in any suitable combinations and/or sub-combinations in one or more embodiments or examples. In addition, it is appreciated that the figures provided herewith are for explanation purposes to persons ordinarily skilled in the art and that the drawings are not necessarily drawn to scale.

As used herein, the terms "comprises," "comprising," "includes," "including," "has," "having," or any other variation thereof, are intended to cover a non-exclusive inclusion. For example, a process, article, or apparatus that comprises a list of elements is not necessarily limited to only those elements but may include other elements not expressly listed or inherent to such process, article, or apparatus.

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these examples or illustrations are utilized will encompass other embodiments which may or may not be given therewith or elsewhere in the specification and all such embodiments are intended to be included within the scope of that term or terms. Language designating such nonlimiting examples and illustrations includes, but is not limited to: "for example," "for instance," "e.g.," and "in one embodiment."

EXAMPLES

The following examples further illustrate the invention.

Example 1

Reaction of Cis-Aconitic Anhydride with α-galactosidase A

A solution of enzyme (α-galactosidase A(α-Gal A)) was prepared at 1.35 mg/ml in 0.95 ml of Buffer A, pH 6.5 (110 mM NaHPO4, 0.22% NaN3, and 0.55 mM PMSF). To this was added 1 mg of cis-aconitic anhydride and stirred in the cold at 4° C. for 1.5 hr. The free anhydride was removed with a Sephadex G25 column.

Activity was measured using the artificial substrate MUG, with modification to use microtiter plates. Briefly, 10 ul of enzyme was mixed with 90 ml of enzyme assay buffer (5 mM MUG, 40 mM of sodium acetate buffer, pH 4.5) at 37° C. and incubated at 37° C. At 0, 10, 30, and 60 min, 10 ul was removed from the incubation mixture and added to 100 ml stop buffer of 0.1 M DAE (Sigma, catalog no. E-1521) in a microtiter plate and the fluorescence was read at excitation of 360 nm and emission of 460 nm. Activity was calculated by averaging the last two readings of the fluorimeter and dividing by the coefficient of the MU standard.

The actual activity of the wild type and modified enzymes were identical within experimental error (57,000 units/ml). Enzyme activity was tested in accordance with Chen et al. 2000.

Example 2

Reaction of Cis-Aconitic Anhydride with HSA

The reaction is carried out in PBS buffer with 2 mg/ml HSA-fluorescein and 10 fold excess cis-aconitic anhydride at pH 8.5 at 25° C. for two hours. The aconitylated-HSA-fluorescein product was separated from free label with Sepandex G-25 chromatography.

Example 3

Conjugation of α-galactosidase A to Fluorescently-Labeled Aconitylated-HSA (aco-HSA)

Fluorescent Labeling of HSA.

First, HSA was labeled with fluorescein. This reaction was carried out in PBS buffer with 2 mg/ml HSA and 20 fold excess NHS-fluorescein at pH 6.5 at 25° C. for one hour to give a low yield labeling reaction (F/P ratio <2) and leave free —NH$_2$ groups for aconitylation reaction. The HSA-fluorescein product was separated from free label with Sepandex G-25 chromatograhy.

Next, cis-aconitic anhydride aconitylation of HSA-fluorescein was done. The reaction was carried out in PBS buffer with 2 mg/ml HSA-fluorescein and 10 fold excess cis-aconitic anhydride at pH 8.5 at 25° C. two hours. The aco-HSA-fluorescein product was separated from free label with Sepandex G-25 chromatograhy.

α-Gal A-PEG3$_{300}$-Maleimide Reaction.

Next, α-galactosidase A is conjugated to PEG3$_{300}$-maleimide. The reaction is carried out in PBS buffer with 2 mg/ml α-Gal A and 20 fold excess SM(PEG)8 (Pierce, catalog number 22108) at pH 8.5 at 25° C. two hours. The α-Gal A-PEG3$_{300}$-maleimide product was separated from free label with Sephadex G-25 chromatograhy.

α-Gal A-PEG3$_{300}$-Maleimide/aco-HSA-Fluorescein Reaction.

Next, α-Gal A-PEG3$_{300}$-maleimide is conjugated to aco-HSA-fluorescein. The reaction is carried out in PBS buffer with 1 mg/ml to 20 mg/ml concentration of α-Gal A-PEG3$_{300}$-maleimide/aco-HSA-fluorescein at 4° C. for two hours. The α-Gal A-PEG$_{300}$-maleimide-Aco-HSA-fluorescein product is separated from free aco-HSA-fluorescein with Sephadex G-200 chromatograhy combined with α-Gal A activity assays of fractions collected.

Example 4

α-galactosidase A and Fluorescently Labeled Aconitylated-HSA Coupled to Multi-Arm PEG (Amino Based Coupling)

8-arm amino multi arm star PEG (Mw 20k) (NANOCS) is functionalized NHS using low pH hydrolyzable Sulfo-EGS(Ethylene glycol bis[sulfosuccinimidylsuccinate]) (pierce 21566). 8-arm $_{PEG20,000}$-NH$_2$ (100 mg/ml) was reacted with 20 fold excess of Sulfo-EGS at 25° C. for 30 minutes followed by G-25 Sephadex chromatography to yield 8-arm PEG$_{20,000}$-NH-EGS.

The 8-arm PEG$_{20,000}$-NH-EGS was reacted at 25° C. for 1 hour with a mixture of equimolar mixture of α-gal-NH$_2$ HSA-NH$_2$ at 2 mg/ml protein concentration, followed by treatment with 6-aminofluorescein (0.2 mg/ml in 5% DMSO). Superdex 200 chromatography is used to separate out the resulting bioconjugates with molecular weights larger than 50 kDa.

Example 5

α-galactosidase A and Fluorescently Labeled Aconitylated-HSA Coupled to Multi-Arm PEG (Sulfhydryl "CYS"-Based Coupling)

8-arm amino multi arm star PEG (Mw 20 k) (NANOCS) is functionalized with NHS using low pH hydrolyzable Sulfo-EGS(Ethylene glycol bis[sulfosuccinimidylsuccinate]) (pierce 21566). Sulfo-EGS and NH$_2$-PEG$_{1000}$-maleimide functionalization of 8-arm PEG$_{20,000}$-NH$_2$ reaction conditions (all at pH 7.5). 8-arm PEG$_{20,000}$-NH$_2$ (100 mg/ml) was reacted with 20 fold excess of Sulfo-EGS at 25° C. for 30 minutes followed by G-25 Sephadex chromatography to yield 8-arm PEG$_{20,000}$-NH-EGS. This intermediate was reacted with NH$_2$-PEG$_{1000}$-maleimide (10 fold excess) at 25° C. for 2 hours followed by G-50 Sehadex chromatography to yield 8-arm PEG$_{20,000}$-NH-EGS -PEG$_{1000}$-maleimide.

The 8-arm PEG$_{20,000}$-NH-EGS-PEG$_{1000}$-maleimide was reacted at 25° C. for 1 hour with a mixture of equimolar mixture of α-Gal A-SH and HSA-SH at 2 mg/ml protein concentration (native free-SH from cysteines), followed by treatment with FITC-PEG$_{1000}$-SH for 1 hour. Superdex 200 chromatography is used to separate out the resulting bioconjugates with molecular weights larger than 50 kDa.

What is claimed is:

1. A composition comprising a lysosomal enzyme directly conjugated to a negatively charged scavenger receptor ligand by way of a hydrolysable linker.

2. The composition of claim 1, wherein said lysosomal enzyme is selected from the group consisting of α-galactosidase A, α-sialidase, α-mannosidase, β-mannosidase, glycosylasparaginase, α-fucosidase, α-N-acetylglucosaminidase, β-galactosidase, β-hexosaminidase, α-subunit, β-hexosaminidase β-subunit, GM2 activator protein, glucocerebrosidase, saposin C, arylsulfatase A, saposin B, formylglycin generating enzyme, β-galactosylceramidase, iduronate sulfatase, α-iduronidase, heparin N-sulfatase, acetyl-CoA transferase, N-acetyl glucosaminidase, β-glucuronidase, N-acetyl glucosamine 6-sulfatase, N-acetylgalactosamine 4-sulfatase, galactose 6-sulfatase, hyaluronidase, α-glucosidase, acid sphingomyelinase, acid ceramidase, acid lipase, cathepsin K, cathepsin A, tripeptidyl peptidase, palmitoyl-protein thioesterase.

3. The composition of claim 1, wherein said lysosomal enzyme is α-galactosidase A.

4. The composition of claim 1, wherein said lysosomal enzyme is recombinant human lysosomal enzyme.

5. The composition of claim 1, wherein said lysosomal enzyme is acylated.

6. The composition of claim 1, wherein said lysosomal enzyme is acetylated.

7. The composition of claim 1, wherein said lysosomal enzyme is aconitylated.

8. The composition of claim 1, wherein said scavenger receptor ligand is acylated.

9. The composition of claim 1, wherein said scavenger receptor ligand is acetylated.

10. The composition of claim 1, wherein said scavenger receptor ligand is aconitylated.

11. The composition of claim 1, wherein said negatively charged scavenger receptor ligand is selected from the group consisting of acetylated low density lipoprotein (AcLDL), oxidized low-density lipoprotein (OxLDL), β-amyloid, molecular chaperones, extracellular matrix (ECM), advanced glycation and products (AGE), apoptotic cells, activated B-cells, bacteria, high density lipoprotein (HDL), low density lipoprotein (LDL), very low density lipoprotein (VLDL), activated platelets, serum protein, bovine serum albumin (BSA), and human serum albumin (HSA).

12. The composition of claim 1, wherein said scavenger receptor ligand is human serum albumin (HSA).

13. The composition of claim 1, further comprising a label.

14. The composition of claim 13, wherein said label is a fluorescent label.

15. The composition of claim 1, wherein said linker further comprises polyethylene glycol (PEG) polysaccharide, poly amino acid, or polyamine.

16. The composition of claim 15, wherein said linker comprises polyethylene glycol (PEG).

17. The composition of claim 16, wherein said polyethylene glycol (PEG) is a multi-arm polyethylene glycol (PEG).

18. The composition of claim 17, wherein said multi-arm polyethylene glycol (PEG) is a star polyethylene glycol (PEG).

19. The composition of claim 16, further comprising a label.

20. The composition of claim 19, further comprising a fluorescent label.

21. A composition comprising lysosomal enzyme encapsulated by a liposome, said liposome externally comprising a negatively charged scavenger receptor ligand.

22. The composition of claim 21, wherein said lysosomal enzyme is selected from the group consisting of α-galactosidase A, α-sialidase, α-mannosidase, β-mannosidase, gly-cosylasparaginase, α-fucosidase, α-N-acetylglucosaminidase, β-galactosidase, β-hexosaminidase, α-subunit, β-hexosaminidase β-subunit, GM2 activator protein, glucocerebrosidase, saposin C, arylsulfatase A, saposin B, formylglycin generating enzyme, β-galactosylceramidase, iduronate sulfatase, α-iduronidase, heparin N-sulfatase, acetyl-CoA transferase, N-acetyl glucosaminidase, β-glucuronidase, N-acetyl glucosamine 6-sulfatase, N-acetylgalactosamine 4-sulfatase, galactose 6-sulfatase, hyaluronidase, α-glucosidase, acid sphingomyelinase, acid ceramidase, acid lipase, cathepsin K, cathepsin A, tripeptidyl peptidase, palmitoyl-protein thioesterase.

23. The composition of claim 21, wherein said lysosomal enzyme is α-galactosidase A.

24. The composition of claim 21, wherein said lysosomal enzyme is recombinant human lysosomal enzyme.

25. The composition of claim 21, wherein said negatively charged scavenger receptor ligand is selected from the group consisting of acetylated low density lipoprotein (AcLDL), oxidized low-density lipoprotein (OxLDL), β-amyloid molecular chaperones, extracellular matrix (ECM), advanced glycation and products (AGE), apoptotic cells, activated B-cells, bacteria, high density lipoprotein (HDL), low density lipoprotein (LDL), very low density lipoprotein (VLDL), activated platelets, serum protein, bovine serum albumin (BSA), and human serum albumin (HSA).

26. The composition of claim 21, wherein said negatively charged scavenger receptor ligand is human serum albumin (HSA).

27. The composition of claim 21, wherein said scavenger receptor ligand is acylated.

28. The composition of claim 21, wherein said scavenger receptor ligand is acetylated.

29. The composition of claim 21, wherein said scavenger receptor ligand is aconitylated.

30. The composition of claim 21, wherein said negatively charged scavenger receptor ligand further comprises a label.

31. The composition of claim 30, wherein said label is a fluorescent label.

32. A method of treating a lysosomal storage disease in a mammal, said method comprising administering to said mammal a therapeutic amount of a pharmaceutical composition comprising lysosomal enzyme directly conjugated to a negatively charged scavenger receptor ligand by way of a hydrolysable linker.

33. The method of claim 32, wherein the lysosomal storage disease is caused by deficient lysosomal enzyme.

34. The method of claim 32, wherein said lysosomal enzyme is α-galactosidase A.

35. The method of claim 32, wherein said disease is Fabry disease.

36. A method of treating a lysosomal storage disease in a mammal, said method comprising administering to said mammal a therapeutic amount of a pharmaceutical composition comprising lysosomal enzyme encapsulated by a liposome, said liposome externally comprising a negatively charged scavenger receptor ligand.

37. The method of claim 36, wherein the lysosomal storage disease is caused by deficient lysosomal enzyme.

38. The method of claim 36, wherein said lysosomal enzyme is α-galactosidase A.

39. The method of claim 36, wherein said disease is Fabry disease.

\* \* \* \* \*

UNITED STATES PATENT AND TRADEMARK OFFICE
CERTIFICATE OF CORRECTION

PATENT NO. : 10,138,474 B2  
APPLICATION NO. : 13/970551  
DATED : November 27, 2018  
INVENTOR(S) : David H. Calhoun et al.

Page 1 of 1

It is certified that error appears in the above-identified patent and that said Letters Patent is hereby corrected as shown below:

In the Specification

<u>Column 2, Line 47</u>:  
Now reads: "and other patients reeving"  
Should read: -- and other patients receiving --

Signed and Sealed this  
Sixth Day of August, 2019

Andrei Iancu  
*Director of the United States Patent and Trademark Office*